US 6,478,730 B1

(12) United States Patent
Bala et al.

(10) Patent No.: US 6,478,730 B1
(45) Date of Patent: *Nov. 12, 2002

(54) ZOOM LAPAROSCOPE

(75) Inventors: John L. Bala, Pomfret Center, CT (US); Paul Remijan, Holland, MA (US)

(73) Assignee: VisionScope, Inc., Waltham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,134

(22) Filed: Sep. 9, 1998

(51) Int. Cl.⁷ .............................. A61B 1/05; A61B 1/07
(52) U.S. Cl. .................... 600/121; 600/125; 600/131; 600/168; 600/171; 600/182
(58) Field of Search ................. 600/129, 121, 600/125, 167, 168, 114, 170, 171, 173, 182, 122–124, 131

(56) References Cited

U.S. PATENT DOCUMENTS

| 3,261,349 | A | | 7/1966 | Wallace | 128/6 |
|---|---|---|---|---|---|
| 3,736,376 | A | | 5/1973 | Kato, Jr. | 178/6.8 |
| 3,794,091 | A | | 2/1974 | Ersek et al. | 150/52 R |
| 3,809,072 | A | | 5/1974 | Ersek et al. | 128/23 |
| 4,074,306 | A | | 2/1978 | Kakinuma et al. | 358/1 |
| 4,253,447 | A | | 3/1981 | Moore et al. | 128/6 |
| 4,261,344 | A | | 4/1981 | Moore et al. | 128/6 |
| 4,364,629 | A | | 12/1982 | Lang et al. | 350/516 |
| 4,488,039 | A | | 12/1984 | Sato et al. | 250/216 |
| 4,558,691 | A | * | 12/1985 | Okada | 600/167 |
| 4,604,992 | A | | 8/1986 | Sato | 128/6 |
| 4,624,243 | A | | 11/1986 | Lowery et al. | 128/6 |
| 4,646,722 | A | | 3/1987 | Silverstein et al. | 128/4 |
| 4,704,007 | A | | 11/1987 | Landre et al. | 350/414 |
| 4,741,326 | A | | 5/1988 | Sidall et al. | 128/4 |
| 4,746,203 | A | | 5/1988 | Nishioka et al. | 350/401 |
| 4,760,840 | A | | 8/1988 | Fournier, Jr. et al. | 128/303.1 |
| 4,768,858 | A | * | 9/1988 | Hussein | 600/114 |
| 4,781,448 | A | | 11/1988 | Chatenever et al. | 350/429 |
| 4,784,118 | A | | 11/1988 | Fantone et al. | 128/6 |

(List continued on next page.)

FOREIGN PATENT DOCUMENTS

| DE | 296 13 103 U1 | 11/1997 |
|---|---|---|
| EP | 0 352 952 | 1/1990 |
| EP | 0 651 272 A2 | 10/1994 |
| WO | 93/25137 | 12/1993 |
| WO | 94/09694 | 5/1994 |
| WO | 94/14367 | 7/1994 |
| WO | 95/02988 | 2/1995 |
| WO | 95/11624 | 5/1995 |
| WO | 95/26674 | 10/1995 |
| WO | 96/10947 | 4/1996 |
| WO | 96/39916 | 12/1996 |
| WO | 97/11634 | 4/1997 |
| WO | 97/14348 | 4/1997 |

*Primary Examiner*—John P. Leubecker
(74) *Attorney, Agent, or Firm*—Bowditch & Dewey, LLP

(57) ABSTRACT

A zoom laparoscope having a laparoscope base unit with a proximal end and a distal end and having a sheath with a zoom assembly. In one embodiment, the laparoscope comprises a two dimensional solid state imaging sensor. The laparoscope can contain a sheath locking mechanism located at both its proximal and distal ends. The sheath can comprise a light transmitting material for illumination of a region of interest. In an alternate embodiment, the sheath comprises an attachment for changing the angle of view of the laparoscope. The laparoscope can also contain a handle at its proximal end.

35 Claims, 11 Drawing Sheets

U.S. PATENT DOCUMENTS

| | | | |
|---|---|---|---|
| 4,819,620 A * | 4/1989 | Okutsu | 600/158 |
| 4,846,155 A | 7/1989 | Kimura | 128/6 |
| 4,858,001 A * | 8/1989 | Milbank et al. | 600/170 |
| 4,860,095 A | 8/1989 | Kimura et al. | 358/98 |
| 4,862,873 A | 9/1989 | Yajima et al. | 128/6 |
| 4,878,485 A | 11/1989 | Adair | 128/6 |
| 4,879,992 A | 11/1989 | Nishigaki et al. | 128/6 |
| 4,947,827 A | 8/1990 | Opie et al. | 128/4 |
| 4,971,035 A | 11/1990 | Ito | 128/6 |
| 4,979,498 A | 12/1990 | Oneda et al. | 128/6 |
| 4,988,172 A | 1/1991 | Kanamori et al. | 350/413 |
| 5,051,824 A * | 9/1991 | Nishigaki | 600/109 |
| 5,058,568 A | 10/1991 | Irion et al. | 128/4 |
| 5,119,189 A | 6/1992 | Iwamoto et al. | 358/88 |
| 5,166,787 A | 11/1992 | Irion | 358/98 |
| 5,191,879 A | 3/1993 | Krauter | 128/4 |
| 5,214,538 A | 5/1993 | Lobb | 359/691 |
| 5,228,430 A | 7/1993 | Sakamoto | 128/6 |
| 5,237,984 A | 8/1993 | Williams, III et al. | 128/4 |
| 5,290,168 A | 3/1994 | Cooper et al. | 433/29 |
| 5,305,098 A | 4/1994 | Matsunaka et al. | 348/65 |
| 5,305,121 A | 4/1994 | Moll | 348/45 |
| 5,329,935 A | 7/1994 | Takahashi | 128/4 |
| 5,337,734 A | 8/1994 | Saab | 128/4 |
| 5,349,941 A | 9/1994 | Hori | 128/4 |
| 5,369,525 A | 11/1994 | Bala et al. | 359/435 |
| 5,379,756 A | 1/1995 | Pileski et al. | 128/6 |
| 5,381,784 A | 1/1995 | Adair | 128/6 |
| 5,386,818 A | 2/1995 | Scheebaum et al. | 128/4 |
| 5,402,768 A | 4/1995 | Adair | 128/4 |
| 5,406,939 A | 4/1995 | Bala | 128/4 |
| 5,413,092 A | 5/1995 | Williams, III et al. | 128/4 |
| 5,418,645 A | 5/1995 | Coath et al. | 359/676 |
| 5,423,312 A | 6/1995 | Siegmund et al. | 128/6 |
| 5,429,118 A | 7/1995 | Cole et al. | 600/121 |
| 5,483,951 A | 1/1996 | Frassica et al. | 600/104 |
| 5,486,155 A | 1/1996 | Muller et al. | 600/137 |
| 5,489,256 A | 2/1996 | Adair | 600/133 |
| 5,494,483 A | 2/1996 | Adair | 600/111 |
| 5,506,912 A | 4/1996 | Nagasaki et al. | 382/103 |
| 5,538,497 A | 7/1996 | Hori | 600/182 |
| 5,547,457 A * | 8/1996 | Tsuyuki et al. | 600/173 |
| 5,551,947 A * | 9/1996 | Kaali | 600/114 |
| 5,573,493 A | 11/1996 | Sauer et al. | 600/121 |
| 5,575,757 A * | 11/1996 | Kennedy et al. | 600/167 |
| 5,582,576 A | 12/1996 | Hori et al. | 600/167 |
| 5,584,793 A * | 12/1996 | Sauer et al. | 600/121 |
| 5,621,830 A * | 4/1997 | Lucey et al. | 600/171 |
| 5,630,784 A | 5/1997 | Siegmund et al. | 600/160 |
| 5,634,881 A | 6/1997 | Francis | 600/138 |
| 5,662,584 A | 9/1997 | Hori et al. | 600/103 |
| 5,700,236 A | 12/1997 | Sauer et al. | 600/175 |
| 5,745,165 A * | 4/1998 | Atsuta et al. | 600/167 |
| 5,751,341 A | 5/1998 | Chaleki et al. | 348/65 |
| 5,762,603 A | 6/1998 | Thompson | 600/112 |
| 5,776,049 A | 7/1998 | Takahashi | 600/111 |
| 5,817,014 A | 10/1998 | Hori et al. | 600/118 |
| 5,817,015 A * | 10/1998 | Adair | 600/121 |
| 6,117,071 A * | 9/2000 | Ito et al. | 600/168 |

\* cited by examiner

ZOOM LAPAROSCOPE

BACKGROUND OF THE INVENTION

Endoscopes are devices which allow visual examination inside a hollow cavity. In the field of medicine, the use of endoscopes permits inspection of organs for the purpose of diagnosis, viewing of a surgical site, sampling tissue, or facilitating the safe manipulation of other surgical instruments. Laparoscopes are used particularly for examining organs in the abdominal area. Laparoscopes typically include a light pipe for illuminating the region to be viewed, at least one lens assembly for focusing and relaying the image of the illuminated object, and a housing for the entire assembly which is structured to minimize tissue damage during the surgical procedure. The light pipe can include a fiber optic element for illuminating the site. The laparoscope housing includes a distal section that can be inserted within a body cavity and a proximal section which can include a handle that a user grips to position the distal end near the surgical site.

Existing laparoscopes can include an imaging device such as a charge coupled device (CCD). This solid state imaging system is used to capture an image of an object being viewed and convey it to a viewing device, such as monitor.

Currently, several problems exist with current laparoscope instruments. In laparoscope devices without a zoom system, in order for the viewer to obtain a closer view of an object, he has to adjust the position of the entire laparoscope manually. There is a risk of damaging or perforating soft tissues when the laparoscope is moved at a surgical site. Laparoscope devices containing zoom lenses also have drawbacks. After zooming on an object to be viewed, the user must focus the lenses on the object to obtain a viewable image. A continuing need exists, therefore, for improvements in endoscopic design to provide safer, more economical, and effective systems for examination of patients.

SUMMARY OF THE INVENTION

The invention relates to an endoscope device, and in a preferred embodiment, to a laparoscope having a tube with a proximal end and a distal end for insertion into body cavities or lumens for viewing of a site. The laparoscope can include, in a preferred embodiment, an illumination device, an imaging device, and a sheath having a lens system. The tube can comprise interlocking mechanisms to connect the sheath to the proximal and distal portions of the tube.

In a preferred embodiment, the illumination device is a fiber optic coupler and the imaging sensor can be a solid state imaging sensor, such as a charge coupled device or a two dimensional CMOS imaging device. The imaging device can be positioned at the distal end tube adjacent to the sheath lens systems.

The laparoscope can also include, in another embodiment, a sheath having a series of lenses that provides a zoom assembly. The laparoscope has a zoom control that actuates the zoom assembly. The zoom control can be mechanically operated, or in another embodiment, the zoom can be motorized. A finger operated switch on the handle can operate the motor or mechanically move the zoom assembly.

The front lens element on the sheath can be an objective lens which has a dual purpose. First, it is used to image the surgical area with the required resolution onto the solid state imaging sensor. Second, it provides a hermetic seal at the end of the sheath. The hermetic seal provides a sterile environment for the laparoscope. In one embodiment, the front lens element is a diffractive lens. Most optical systems of existing laparoscopes use four to six lenses to image the surgical area onto a camera. Each lens surface reflects as much as 4% of the incident light reaching the lens surface. Because these losses are cumulative, a six element objective lens can lose as much as 36% of the light from an image. A diffractive lens system can use only one lens and can have a loss of only about 8% of the light from an image.

The sheath with the zoom assembly can comprise a plastic having an index of refraction and an inner and outer layer of a lower index of refraction plastic. The sheath can also comprise a plurality of lenses as part of its zoom assembly. In a particular embodiment, there are four lenses in the optical system for the zoom assembly. In one aspect of this embodiment of the invention, the sheath includes a moveable inner sleeve and a stationary inner sleeve as part of its zoom assembly. The second and fourth lenses are mounted to the moveable sleeve and the first and third lenses are mounted to the stationary sleeve. During a zooming procedure, the second and fourth lenses translate linearly while the third lens element is caused to rotate within its housing by a cam mechanism. An advantage of this apparatus is that it is not necessary to focus the lenses following actuation of the zoom lens assembly to adjust the magnification. Thus the image of a particular region of interest can be magnified or demagnified to show a wider field of view without adjusting the focus of the optical system.

In a preferred embodiment, the lenses can comprise a molded plastic material. Existing laparoscopes incorporate expensive ground glass lenses in structures that are complicated and difficult to manufacture. Because of this, it has not been possible to manufacture laparoscopes or laparoscope components containing precision optics which are disposable and economically feasible for the user. Because the lenses of the present invention are plastic and relatively inexpensive, the sheaths having the zoom lens assembly are disposable after a single procedure and thereby reduce the sterilization needs for the system.

The invention can also include a sheath for changing the angle of view of an endoscope. The distal portion of the sheath can house the structure for changing the angle of view. In a preferred embodiment, this structure includes a prism. Viewing angles can be provided, preferably, between 30 and 45 degrees, however other angles an be used.

In a preferred embodiment, the laparoscope can include a handle at the proximal end of the system which the user can grasp and manipulate with one hand. The handle can comprise two portions attached by a connector which hermetically seal the proximal end. The handle surface can also comprise a plurality of surface ridges and depressions. The handle allows the proximal end of a laparoscope to remain sterile during a surgical procedure. The handle can be made from plastic, allowing for economic disposal after the laparoscopic procedure is completed. The connector can be disengaged using a push button manual release. The handle permits one-handed use of the laparoscope, allowing the user a free hand to perform other tasks.

The invention further relates to a method of using a laparoscope and sheath assembly. The method involves placing a sheath on a laparoscope, placing the laparoscope within a surgical area, adjusting a zoom control to view an object and removing the laparoscope from the surgical area. The sheath can then be removed from the laparoscope and replaced with a sterile sheath. The method can then be repeated for a different patient while maintaining the sterility of the instrument.

In another preferred embodiment of the invention the laparoscope tube and the sheath can be flexible so that the user can orient the tube in a curved shape to afford viewing at a different angle. This embodiment can employ a distally mounted zoom assembly optically coupled to an imaging sensor as described previously herein. The sheath and inner tube of the assembly are made with a flexible hermetically sealed tubes having a shape memory so that the user can manually manipulate the flexible section into the desired shape and insert the distal end into a bodily cavity without losing the shape. The system can also incorporate cable or other mechanical or motorized elements so that the user can reposition the distal flexible section while still within a cavity during a procedure.

Figure 1:
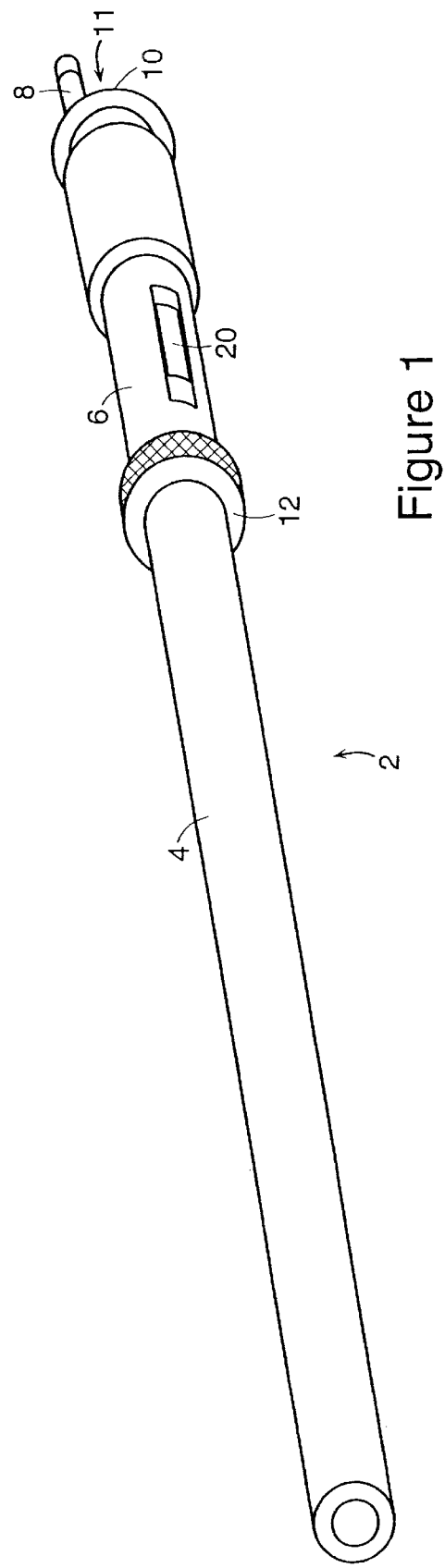
FIG. 1 is an orthogonal view of one embodiment of a laparoscope with sheath assembly in accordance with the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention is illustrated in FIG. 1. A laparoscope and sheath assembly 2 can be used, for example, in minimally invasive surgical procedures involving examination of the abdomen and abdominal organs. The assembly 2 contains both a laparoscope base unit 6 and a laparoscope sheath 4. The laparoscope sheath 4 contains a zoom assembly, manipulated by a zoom control 20, which allows a user to obtain an enlarged view of an object during a laparoscopic surgical procedure without having to adjust the position of the laparoscope inside the patient.

Figure 2:
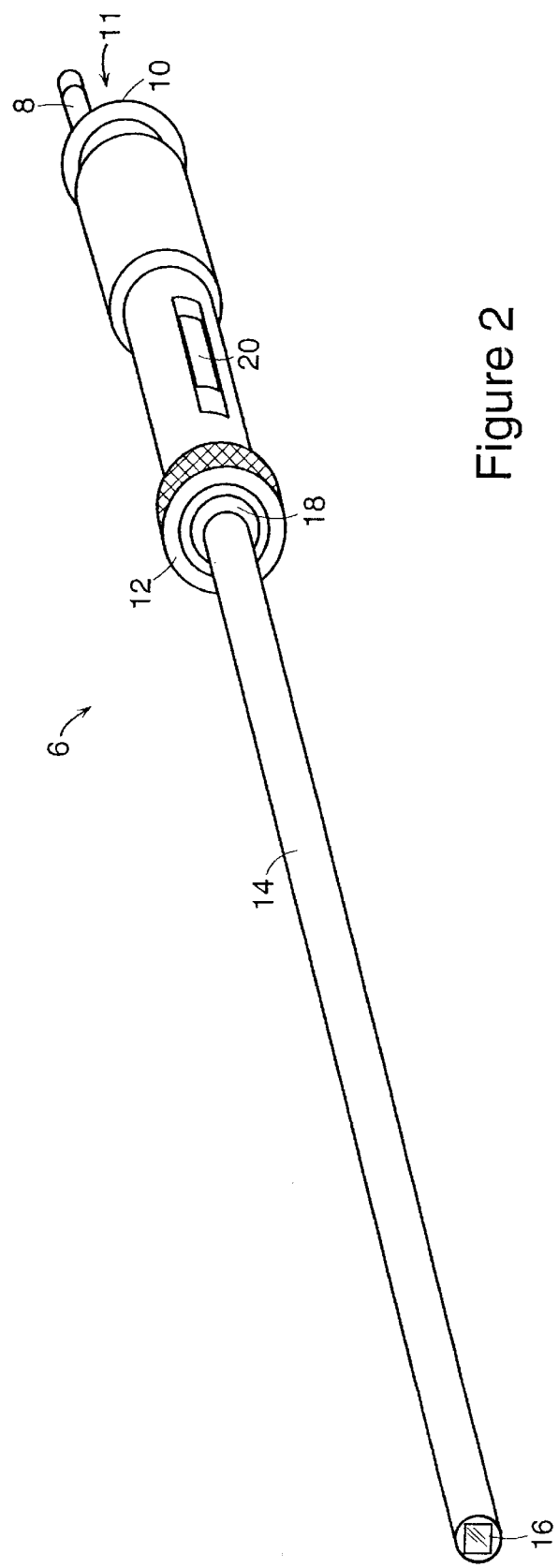
FIG. 2 is an orthogonal view of an embodiment of a laparoscope base unit.

FIG. 2 shows an embodiment of a laparoscope base unit 6 which includes a probe or tube 14, a light source connector 8, an electrical source connector 10, an illumination coupling device 18, a proximal interlocking device 12, a zoom control 20, and an imaging device 16. The probe 14 of the laparoscope base unit 6 allows viewing of the inside of a physiologic cavity. The probe 14 is hollow to allow for inclusion of an imaging device. The probe 14, in a preferred embodiment, is composed of stainless steel. In an alternate embodiment, the probe 14 is composed of any biologically compatible and sterilizable material. The probe 14 is elongated, having a diameter in the range between 6.8 mm and 7.2 mm and is between 350 mm and 420 mm in length. In one example of a preferred embodiment, the length of the probe 14 can be 390 mm.

In one embodiment, the laparoscope base unit 6 contains both a light source connector 8 to provide the laparoscope assembly 2 with light from an outside source and an electrical connector 10 which provides the laparoscope assembly 2 with power from an external source. The light source connector 8 is located at the proximal end of the laparoscope 6. In a preferred embodiment, the light source connector 8 is mounted to the rear face 11 of the laparoscope 6 and is parallel to the probe 14 to allow for ease of handling the laparoscope assembly 2. In an alternative embodiment, the laparoscope assembly 2 can contain an internal lighting and power source. The illumination device 18 of the laparoscope base unit provides light to the distal end of the laparoscope and sheath assembly 2. The illumination device 18 is coupled to the light source connector 8 at the proximal end of the laparoscope and sheath assembly 2. In a preferred embodiment, the illumination device 18 is a fiber optic annulus.

In one embodiment, the proximal interlocking device 12 is located on the laparoscope base unit 6 and secures the sheath 4 to the proximal end of the base unit 6 to maintain its sterility. In a preferred embodiment, the interlocking device 12 is a split ring collar which surrounds the sheath and, when engaged, creates pressure on the sheath 4 without breaking the outer surface of the sheath 4. The laparoscope base unit 6 also contains a zoom control 20. The zoom control 20 allows the user to adjust the position of the tube 14 which is connected to a series of lenses, thus allowing the user to adjust the image of an object being viewed. In one embodiment, the zoom control 20 is located at the proximal end of the laparoscope base unit 6 to allow easy access during a surgical procedure. In a preferred embodiment, the zoom control 20 is operated manually as a sliding mechanism. The zoom control 20 has a range of motion sufficient to allow magnification and demagnification of an object being viewed. In an alternate embodiment, a rotating mechanism can be used. In another embodiment, a motorized mechanism can function as the zoom control 20.

The laparoscope base unit 6 contains an imaging device 16 connected to the electrical source connector 10. The imaging device 16 includes a two dimensional solid state imaging sensor. In a preferred embodiment, the imaging device 16 is a charge coupled device (CCD) camera. The CCD camera has a resolution of at least 9 microns and provides high resolution visual detail of the surgical area being examined. In a preferred embodiment, the imaging device 16 is located at the distal end of the probe 14. Once the imaging device 16 is mounted at the distal end of the probe 14, the end can be sealed by coupling an IR filter to the end of the probe 14. By positioning the imaging sensor at the distal end, this minimizes optical losses in the system and simplifies the optical design.

Figure 3:
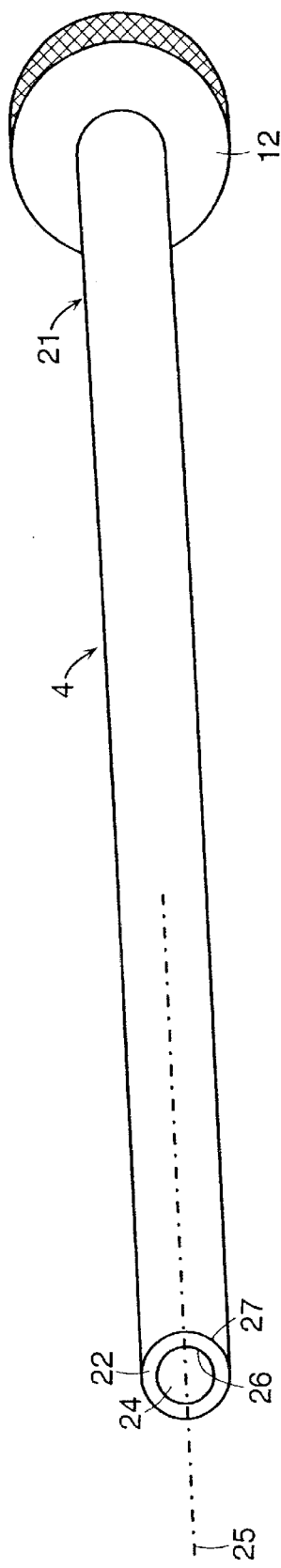
FIG. 3 is an orthogonal view of a laparoscope sheath.

FIG. 3 illustrates an embodiment of the laparoscope sheath 4. The sheath 4 comprises a center layer 22 and an inner 26 and outer 27 layer. The center layer 22, in a preferred embodiment, is composed of medium index of refraction plastic. The center layer 22 transmits light from the illumination device 18 located in the proximal end of the laparoscope base unit 6 to the surgical area of interest. The center layer material is formed using co-extruded plastic technology to form a light rod 22. The light rod 22 is cut to a specific length with a tool designed to create a lens at each end of the rod 22. In a preferred embodiment, the rod 22 is polyolefin. The inner 26 and outer 27 layers of the sheath 4 are composed of low index of refraction plastic. In a preferred embodiment, the inner 26 and outer 27 layers can be Teflon. Because the sheath is composed of one or more plastic materials the sheath 4 is relatively inexpensive to replace and is therefore disposable. In a preferred embodiment, the sheath 4 comprises a proximal interlocking device 12 located at its proximal end 21 to allow a secure connection between the sheath 4 and the laparoscope base unit 6. In this preferred embodiment, the proximal interlocking device 12 is also used to rotate the sheath 4 about its longitudinal axis 25.

In a preferred embodiment, the sheath 4 comprises an objective lens 24 hermetically sealed to its distal end. The objective lens 24 is preferably a diffractive lens element. The use of the diffractive lens element allows use of the laparoscope and sheath assembly 2 without an optical low pass filter. The diffractive element acts as a filtering component. The use of a diffractive lens element without an optical low pass filter allows the operator to more closely approach the object being viewed with the diffractive lens.

Figure 4:
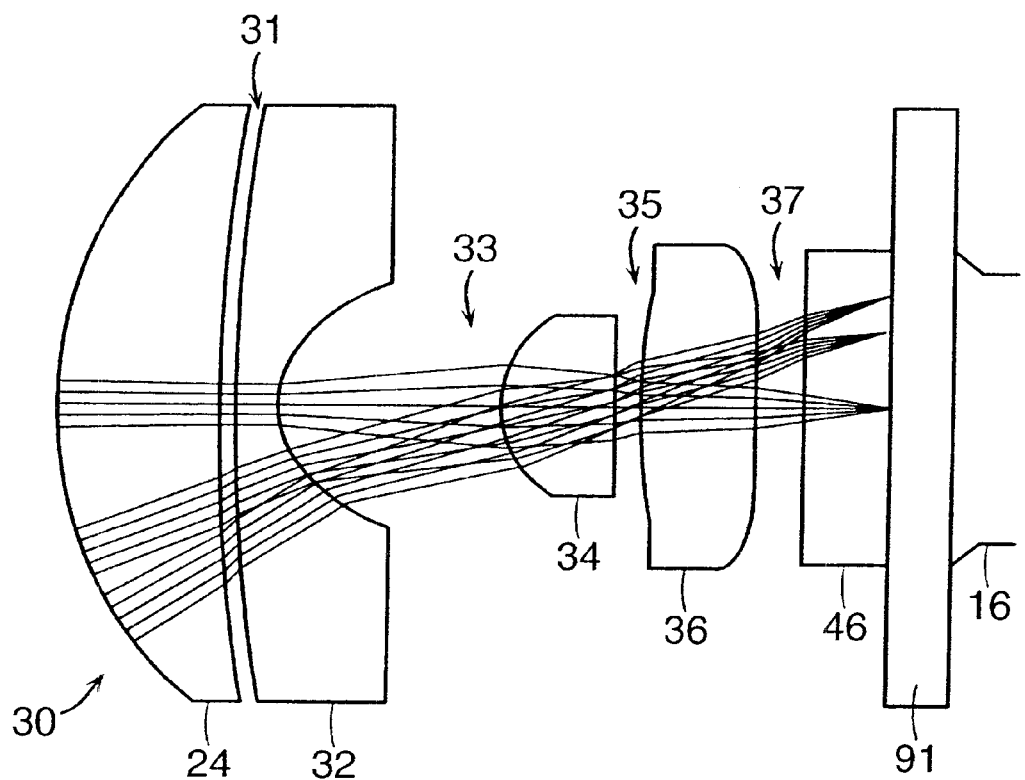
FIG. 4 is a lateral view of a lens series positioned in standard viewing mode.
Figure 5:
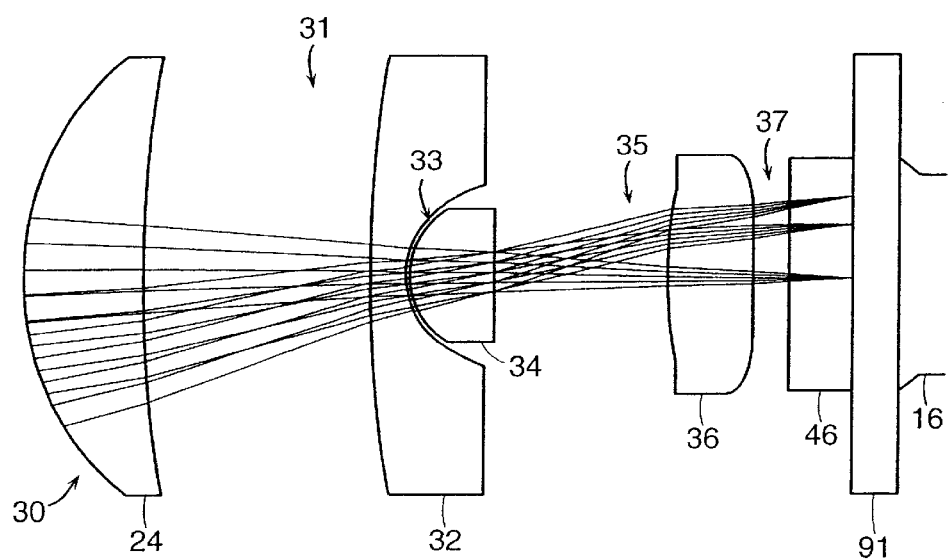
FIG. 5 is a lateral view of a lens series positioned in full zoom mode.

In a preferred embodiment, the sheath 4 contains a lens series 30. FIGS. 4 and 5 show an embodiment of four lenses. The lens series 30 includes an objective lens 24, a first lens spacing 31, a second lens element 32, a second lens spacing 33, a third lens element 34, a third lens spacing 35, a fourth lens element 36, and a fourth lens spacing 37. In a preferred embodiment, the second lens element 32 is a zoom element. In another preferred embodiment, the third lens element 34 and the fourth lens element 36 are aspheric lenses. The fourth lens element 36 is mounted next to an IR filter 46 which is adjacent an imaging device 16, both of which are attached to the laparoscope base unit 6. FIG. 4 illustrates the lens series 30 arranged to provide a wide view of an object being observed. In this particular arrangement, the first lens spacing 31 is, for example, 0.1833 mm, the second lens spacing 33 is 2.5919 mm, the third lens spacing 35 is 0.070 mm and the fourth lens spacing 37 is 0.7532 mm. For this preferred embodiment, the lens series 30 as arranged can provide between a 70 to 85 degree maximum field of view, with a preferred field of view of 72 degrees. FIG. 5 illustrates the lens series 30 arranged to provide a full zoom view of an object being observed. In this particular arrangement, the first lens spacing 31 is 3.5546 mm, the second lens spacing 33 is 0.0595 mm, the third lens spacing 35 is 0.070 mm and the fourth lens spacing 37 is 2.7896 mm. In this embodiment, the lens series 30 as arranged can provide between a 14 to 18 degree minimum field of view, with a preferred field of view of 15.6 degrees. In comparing FIG. 4 with FIG. 5, the lens spacings 31, 33, 35 change when the lens series 30 moves from a wide view arrangement to a full zoom arrangement.

FIGS. 4 and 5 also illustrate a ring 91. The ring 91 is attached to the second 32 and fourth 36 lens elements of the lens series 30. The ring 91 allows the second 32 and fourth 36 lens elements to be rotated within the sheath 4 by an external mechanism. In one embodiment, the external mechanism is a second sheath placed over the sheath 4 containing the lens series 30 and attached to the ring 91. Rotating the second sheath rotates the ring 91 which, in turn, rotates the second 32 and fourth 36 lens elements.

Figure 6:
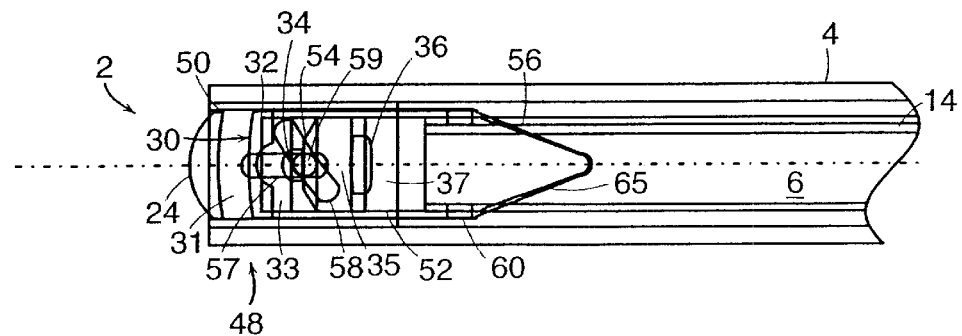
FIG. 6 shows a lateral cross-sectional view of an embodiment of the laparoscope and sheath assembly with a zoom assembly.

FIG. 6 illustrates a cross-sectional view of the distal end of a laparoscope and sheath assembly 2. FIG. 6 shows the manner in which the lens series 30 is mounted within the sheath 4 to form a zoom assembly 48. In a preferred embodiment, the zoom assembly 48 contains the lenses 24, 32, 34, 36 of the lens series 30 having lens spacings 31, 33, 35, 37, respectively, a first sleeve 50, a second sleeve 52, a second lens guide slot 57 located in the surface of the first sleeve 50, and a third lens element housing 54 having a cam pin 59 which slides within a cam slot 58 located in the second sleeve 52.

The sheath 4 surrounding the laparoscope tube 14 can be a plastic illumination element that is optically coupled to the annular array of fibers or rod to provide a light source for viewing at the distal end of the sheath 4.

The lenses of the lens series 30, in a preferred embodiment, are made from optical grade polyurethane which reduces the weight of the lens series 30 within the zoom assembly 48. The objective lens 24 is attached to the first sleeve 50, located on the inside surface of the distal end of the sheath 4, with a hermetic seal. In a preferred embodiment of the invention, the objective lens 24 is attached to the inner surface of the distal end of the sheath 4 to form a hermetic seal. The hermetic seal at the distal end of the sheath 4 allows the laparoscope base unit 6 to remain sterile during a laparoscopic procedure.

The first sleeve 50, located at the distal end of the sheath 4, is connected to the objective lens 24 and the third lens element housing 54 containing the third lens element 34. The first sleeve 50, in a preferred embodiment, is stationary. A second sleeve 52 is also located at the distal end of the laparoscope sheath 4. The second lens element 32 and fourth lens element 36 are mounted on the second sleeve 52. The second sleeve 52, in a preferred embodiment, is adjustable and is connected to a distal sheath interlocking mechanism 56 which is located on the end of the laparoscope base unit 6.

The laparoscope 6 has an angle guide 65 and arms 60 as part of the distal sheath interlocking mechanism 56, located at the distal end of the laparoscope 6. Once the laparoscope sheath 4 is placed over the laparoscope 6, the angle guide 65 and arms 60 aid in properly orienting and locking the sheath 4 onto the laparoscope 6. The angle guide 65 comprises a slot in the laparoscope 6 to receive the proximal end of the second sleeve 52 of the laparoscope sheath 4 and maneuvers the second sleeve 52 into a locking position. The arms 60 extend laterally on opposite sides of the distal end of the laparoscope 6. The proximal end of the second sleeve 52 contains locking slots for engaging the arms 60 and locking the distal end of the sheath 4 to the laparoscope 6. The proximal end of the second sheath 52 slides and "snap" fits over the arms 60, thus securing the distal end of the sheath 4 onto the laparoscope. The arms are preferably spring loaded, allowing for easy installation and removal of the sheath 4. In this embodiment, the arms 60 can be released by the user with a switch at the proximal end.

The zoom assembly 48 is adjusted by the zoom control 20 located at the proximal end of the laparoscope base unit 6.

The zoom control is in contact with the tube 14 of the laparoscope base unit 6. Activation of the zoom control 20 causes the tube 14 to translate. Because the second sleeve 52 is coupled to the distal end of the tube 14, any motion of the tube 14 causes the second sleeve 52 to translate along the long axis of the laparoscope and sheath assembly 2. This motion, in turn, causes the second lens element 32 and the fourth lens element 36 to translate. During the zooming procedure, the third lens element 34 is forced to rotate within its housing 54. The cam slot 58, located in the second sheath 52, drags the cam pin 59 which is mounted in the cam slot 58 and connected to the third lens element 34. By virtue of the shape of the cam slot 58, the third lens element 34 rotates during a zooming procedure.

Allowing the second 32 and fourth 36 lens elements to translate and the third lens element 34 to rotate during a zooming procedure circumvents the necessity of the user to further focus the lenses of the lens series 30 once the procedure is complete. The zoom assembly 48 retains its focus whether in full view mode or full zoom mode. In a preferred embodiment, the zoom assembly 48 travels between 5 mm and 10 mm over the fall zoom range during a zooming procedure.

Figure 7:
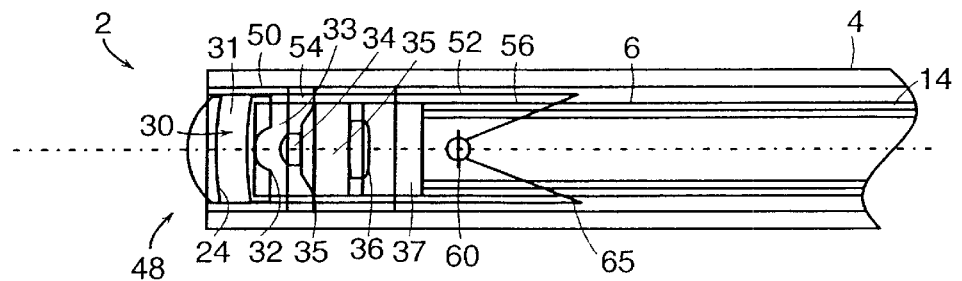
FIG. 7 shows a cross-sectional view of an embodiment of the laparoscope and sheath assembly with a zoom assembly.

FIG. 7 shows a cross-sectional view of the distal end of a laparoscope and sheath assembly 2, rotated 180 degrees from the view shown in FIG. 6. The zoom assembly 48 contains the lenses 24, 32, 34, 36 of the lens series 30 having lens spacings 31, 33, 35, 37, a first sleeve 50, a second sleeve 52, and a third lens element housing 54 mounted. The first sleeve 50 comprises the first 24 and third 34 lens elements and is located within the distal end of the laparoscope sheath 4. The second sleeve 52 comprises the second 32 and fourth 36 lens elements and is connected to a distal sheath interlocking mechanism 56, located on the distal end of the laparoscope base unit 6.

Figure 8:
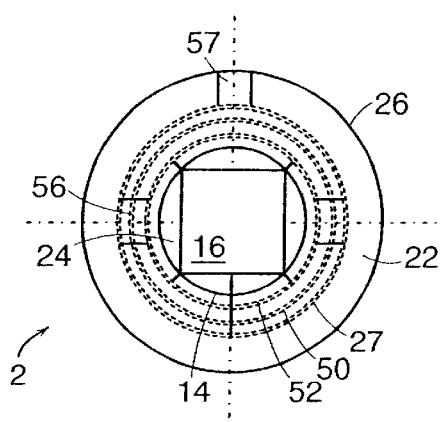
FIG. 8 shows a cross-sectional view of an embodiment of the laparoscope and sheath assembly with a zoom assembly.

FIG. 8 illustrates a front view of the arrangement of the sheath 4 and the laparoscope base unit 6 when assembled as a laparoscope and sheath assembly 2. The assembly 2, as illustrated, comprises a laparoscope base unit 6 having a probe or tube 14, an imaging device 16, and a distal sheath interlocking mechanism 56. The assembly 2 also comprises a sheath 4 composed of a light rod 22 with an outer 26 and an inner 27 sheath coating and having an objective lens 24, a first sleeve 50, a second sleeve 52, and a guide slot 57.

Figure 9:
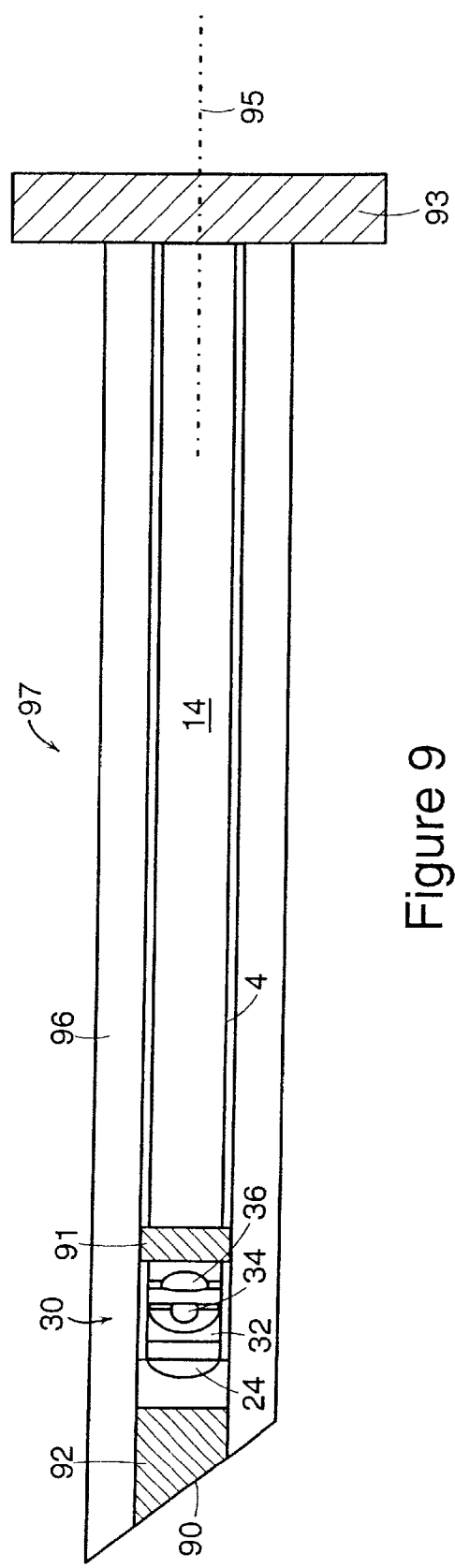
FIG. 9 illustrates a cross-sectional view of an embodiment of a laparoscope sheath having a prism mounted on its distal end.

FIG. 9 shows an alternate embodiment for a laparoscope sheath 97. In this embodiment, the laparoscope sheath 97 comprises a prism 92 mounted to its distal end and a rotational adjustment 93. The prism face 90, in a preferred embodiment, is angled between 22.5 and 45 degrees relative to longitudinal axis 995. When rotated about the longitudinal axis 95, the prism 92 provides the user with a 360 degree view of the surgical area being examined. In one embodiment, the user can rotate the laparoscope and sheath assembly 2 manually to obtain the 360 degree view. A rotational adjustment 93, however, can be used to rotate the prism sheath 97 about the axis 95. The rotational adjustment 93 can be located at the proximal end of the sheath 97 and, in a preferred embodiment, the rotational adjustment 93 is positioned so as to allow the user easy access, by means of the user's thumb or fingers, when operated using a one-handed method.

The sheath 97 is attached to the laparoscope 6 by a ring 91 which can rotate around the axis 95 of the laparoscope 6. The ring 91 is connected to the second 32 and fourth 36 lens elements of the lens series 30. When the sheath 97 is rotated by the user, the ring 91 causes the second 32 and fourth 36 lens elements to rotate.

The prism sheath 97, as illustrated in FIG. 9, fits over a laparoscope sheath having a zoom assembly 48. In this embodiment of the invention, the sheath 97 can be composed from a light pipe 96 to allow illumination of the area being examined. In an alternate embodiment, the prism 92 can be directly attached to a laparoscope sheath having a zoom lens assembly 48. A single sheath combining both the prism 92 and the zoom lens assembly 48 can be used rather than using two separate sheaths. A rotational element 93 can still be used to rotate the prism 92 to obtain a 360 degree view of the area being examined. Similarly, the sheath is attached to a ring 91 which causes the second 32 and fourth 36 lens elements of the lens series 30 to rotate with the prism 92.

Figure 10:
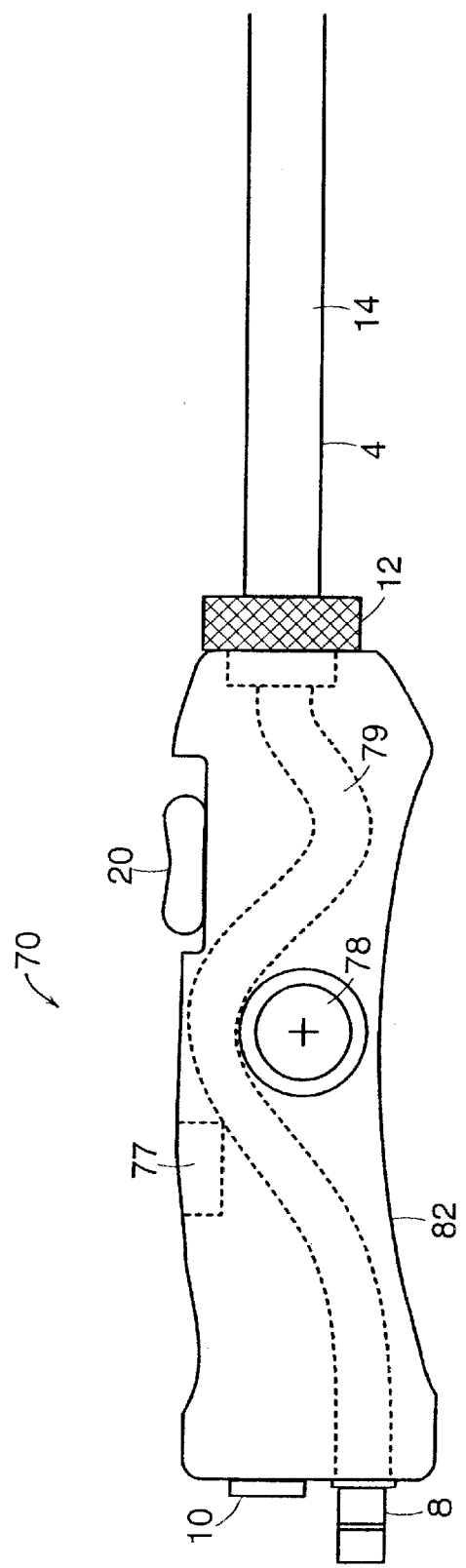
FIG. 10 illustrates a lateral view of an embodiment of the distal end of a laparoscope.
Figure 11:
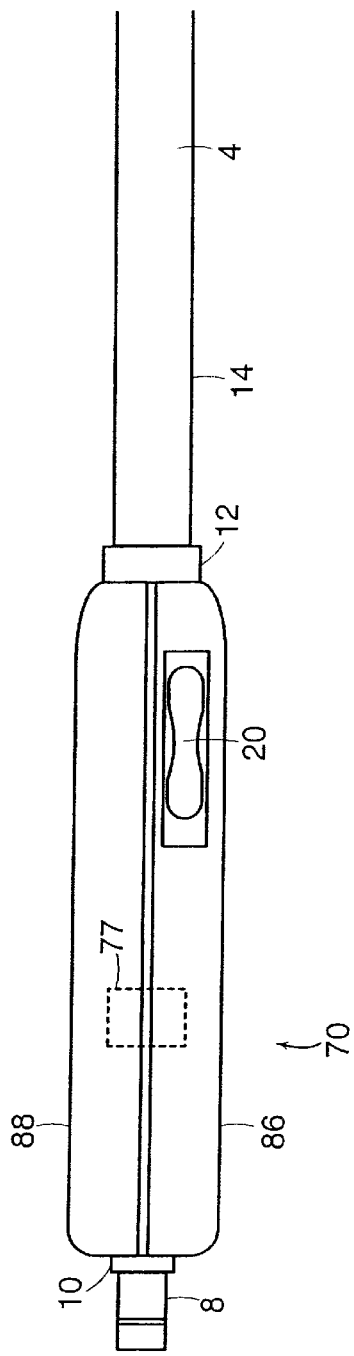
FIG. 11 shows a top view of an embodiment of the distal end of a laparoscope.
Figure 12:
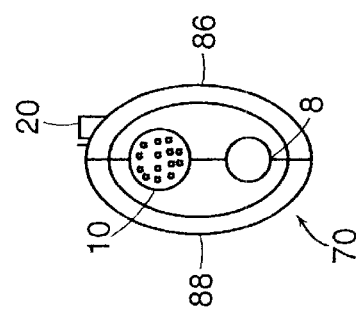
FIG. 12 shows a rear view of an embodiment of the distal end of a laparoscope.

FIGS. 10, 11 and 12 show a lateral, overhead, and rear view, respectively, of the proximal end of a laparoscope and sheath assembly 2. In one embodiment, the proximal end of the assembly 2 contains a handle 70, an electrical connector 10, an illumination connector 8, a fiber optic coupling, a zoom adjustment, and a proximal interlocking device 12.

One purpose of the handle 70 is to maintain the sterility of the proximal end of the laparoscope base unit 6. In one embodiment, the handle 70 is disposable. The handle 70 preferably comprises a right handle portion 86 and a left handle portion 88. These portions 86, 88 are joined by a connector device 77. In one embodiment, the connector device 77 is a mechanical connector triggered by an external control 78. Another purpose of the handle 70 is to provide ease of use of the laparoscope. The handle can have a knife shaped handle surface 82 in one embodiment. This surface 82 allows the user to easily grasp the laparoscope in using either his right or left hand. The surface 82 also allows users with varying hand sizes to comfortable grip the laparoscope.

The fiber optic coupling 79 connects the illumination connector 8 to the illumination device 18 of the laparoscope base unit 6. The fiber optic coupling 79 is mounted within the handle 70 to accommodate rotational motion of the coupling 79 in conjunction with rotation of element 12.

A zoom control 20 is mounted to the handle 70 and connected to the lens system in the laparoscope tube 14. The zoom lens control 20 is a sliding-type control and is shaped so that a user may easily and one-handedly manipulate the control 20 with his thumb or other digits. In a preferred embodiment, there is a 5 mm total travel distance possible for the zoom control.

The proximal end of the laparoscope and sheath assembly 6 also contains an interlocking device 12. In a preferred embodiment, the interlocking device 12 is a collar which surrounds the sheath and, when engaged, creates pressure on the sheath 4 without breaking into the outer surface. The interlocking device 12, in a preferred embodiment, can be secured and loosened by a user utilizing only one hand.

Figure 13:
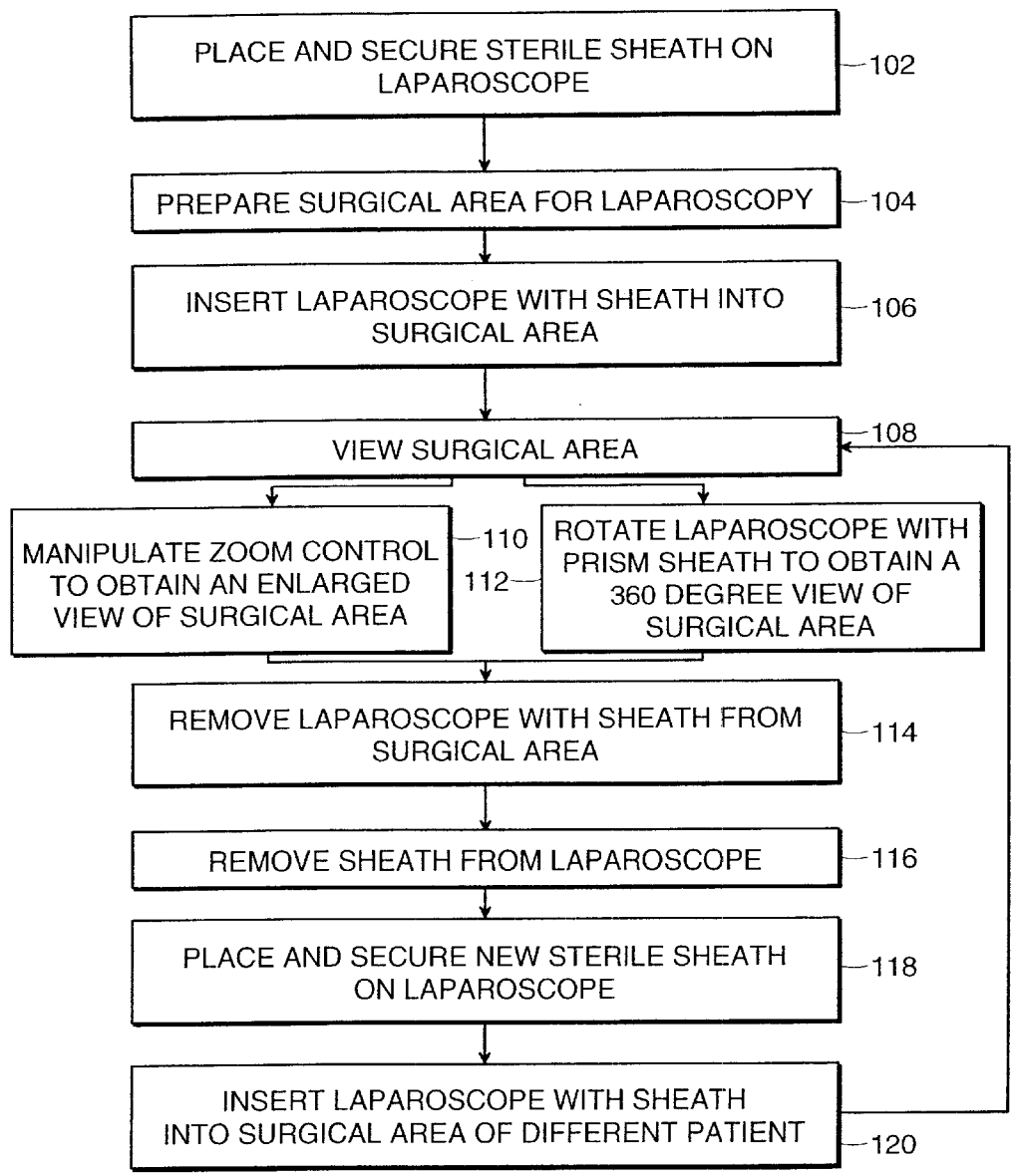
FIG. 13 is a schematic representation of a method for using a laparoscope and sheath assembly.

FIG. 13 illustrates a schematic representation of a method for using a laparoscope and sheath assembly 100. The user places and secures a sterile sheath on the laparoscope 102. The sheath covers the tube of the laparoscope and connects to the laparoscope at both its distal and proximal ends. A pin and an angled pin guide are located at the distal end of the laparoscope. These devices force the sheath into a particular orientation on the laparoscope and secure the sheath to the distal end of the tube. A locking mechanism connects the sheath to the proximal end of the laparoscope. A surgical area is prepared for a laparoscopic procedure by the user 104. The user inserts the laparoscope with sheath assembly into a surgical area 106. The laparoscope provides the user with a minimally invasive view of a physiologic cavity. The surgical area can then be viewed using the laparoscope and sheath assembly. An imaging sensor is used to provide the image from the surgical area to a display device for viewing 108 by the user. Depending on the type of sheath used, the user can either zoom on an object being viewed 110 or obtain a 360 degree view of the object by rotating the sheath. Once the surgical procedure is completed, the laparoscope and sheath assembly is removed from the surgical area 114. The sheath can then be removed from the laparoscope 116. If the laparoscope is needed for another surgical procedure, a new sterile sheath can be placed and secured on the laparoscope 118. The laparoscope and sheath assembly can then be inserted into the surgical area of a different patient 120. By using a new sterile sheath for each procedure, the laparoscope unit does not have to be sterilized after each operation if contamination is limited. This method can be repeated for subsequent patients while maintaining the sterility of the laparoscope unit.

In another embodiment, the zoom lens assembly, the prism, or both can be mounted within a non-disposable, reusable housing rather than in a single disposable or multiple disposable sheaths. A non-disposable and reusable housing requires that the housing be sterilized between uses. In a preferred embodiment, the housing is stainless steel.

Figure 14:
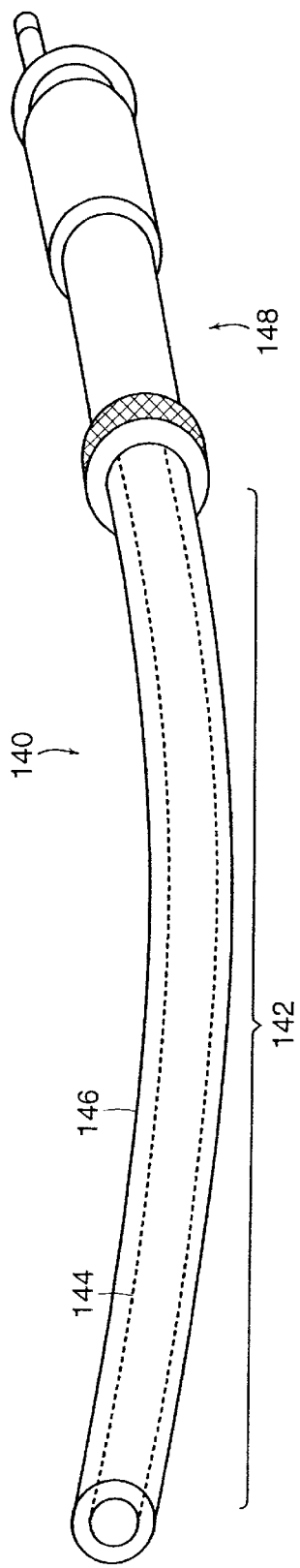
FIG. 14 illustrates a flexible sheath laparoscopic system.

In another preferred embodiment of the invention, the laparoscope 140 includes a flexible probe 144 and a flexible sheath 146 extending over the flexible tube. This embodiment is illustrated in FIG. 14. The laparoscope probe or tube 144 can have a flexible outer surface that retains the described shape. Both the tube 144 and the sheath 146 can have a flexible region 142 which the user can manually manipulate to achieve a desired shape. The tube 144 can be an accordion type cover to provide flexibility and the sheath 146 can be formed with a material having shape memory such that the user can bend the structure to have a particular angular shape for viewing of sites within a body at different angles. Mechanical cables of other mechanical elements can also be used to manually manipulate the angular orientation of the tube. A flexible extruded plastic can be used to couple light from the source to the distal end of the device. In a preferred embodiment, the flexible tube 144 is optically transmissive polyurethane, manufactured by Hercules Corporation, Wilmington, Del. The flexible system can also use a two dimensional solid state sensor array at the distal end of the probe and a zoom assembly at the distal end of the sheath. The flexible system can also employ the optical and mechanical coupling features described previously in the application. The handle 148 can be the two piece disposable assembly described previously herein.

Alternatively, the flexible system can be a non-disposable system that is reused after each procedure following sterilization.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A probe laparoscope comprising:
   a tube having a proximal end and a distal end, the tube being attached to a handle to provide a laparoscope base including a lens system optically coupled to a two dimensional solid state electronic imaging device positioned in the laparoscope base;
   a sheath having a proximal end and a distal end, a channel in which the tube can be inserted, an optical lens element mounted on the distal end of the sheath such that an image of an object is directed through the optical lens element and the lens system that define an optical path onto the imaging device, the image being viewed with the laparoscope, the sheath including an illumination channel that is concentric about the optical path and coupled to a light source; and
   an interlocking mechanism detachably connecting the handle to the proximal end of the sheath.

2. The laparoscope of claim 1 further comprising a zoom control.

3. The laparoscope of claim 2 wherein the zoom control is located at a proximal end of the laparoscope.

4. The laparoscope of claim 2 further comprising a manually operated control that actuates a zoom assembly.

5. The laparoscope of claim 4 wherein the zoom control further comprises a slide mechanism.

6. The laparoscope of claim 4 further comprising a rotating mechanism.

7. The laparoscope of claim 2 further comprising a motor that actuates the zoom assembly.

8. The laparoscope of claim 1 wherein the illumination channel comprises a fiber optic device that is concentric about the tube and the light source is optically coupled to a fiber optic coupler.

9. The laparoscope of claim 1 wherein the imaging device comprises a charge coupled device.

10. The laparoscope of claim 1 wherein the sheath further comprises a center layer of a first index of refraction plastic and an inner layer and an outer layer, each comprising a plastic having a lower index of refraction than the center layer.

11. The laparoscope of claim 1 wherein the sheath comprises a light transmitting material.

12. The laparoscope of claim 1 further comprising an objective lens attached to the distal end of the sheath.

13. The laparoscope of claim 1 further comprising a prism attached to the distal end of the sheath.

14. The laparoscope of claim 1 further comprising an optical system within the tube having a series of at least four lenses including a first lens element, a second lens element, a third lens element and a fourth lens element.

15. The laparoscope of claim 14 wherein the first lens element comprises an objective lens.

16. The laparoscope of claim 14 wherein the first lens element comprises a diffractive element.

17. The laparoscope of claim 14 wherein at least one of the lenses comprises a plastic material.

18. The laparoscope of claim 14 further comprising a zoom assembly having a moveable internal sleeve and a stationary internal sleeve.

19. The laparoscope of claim 18 wherein the moveable internal sleeve is secured to the distal end of the tube.

20. The laparoscope of claim 18 further comprising at least one lens element mounted to the stationary internal sleeve.

21. The laparoscope of claim 18 wherein the first lens element and the third lens element are mounted to the stationary internal sleeve.

22. The laparoscope of claim 21 wherein the third lens element rotates relative to the tube during a zooming procedure.

23. The laparoscope of claim 21 wherein the first lens element and the third lens element travel between 5 mm and 10 mm during a zooming procedure.

24. The laparoscope of claim 18 further comprising at least one lens element mounted to the moveable internal sleeve.

25. The laparoscope of claim 18 wherein the second lens element and the fourth lens element mounted to the moveable internal sleeve.

26. The laparoscope of claim 1 further comprising a handle release mechanism.

27. The laparoscope of claim 1 wherein the handle comprises a plastic material.

28. The laparoscope of claim 1 wherein the handle comprises a first handle portion and a second handle portion attached by a connector.

29. The laparoscope of claim 28 wherein the connector is released by a switch.

30. The laparoscope of claim 1 further comprising a plurality of surface ridges and depressions on the handle.

31. A method for viewing through a an endoscope comprising:

placing an endoscope sheath on an endoscope, body to form an endoscope, the body having a tube and a handle with an optical lens system optically coupled to a two dimensional solid state electronic imaging device, the sheath being detachably connected to the handle with an interlocking device on a proximal end of the sheath and a lens on a distal end of the sheath;

positioning the endoscope sheath and body within a body cavity, the sheath having an illumination channel that is concentric about the distal optical lens and is coupled to a light source, and viewing an object with the endoscope.

32. The method of claim 31 further comprising attaching the endoscope to an external viewing device.

33. The method of claim 31 further comprising attaching the endoscope to an external light source with a fiber optic device in the handle.

34. The method of claim 31 further comprising attaching a prism to the distal end of the endoscope sheath.

35. The method of claim 34 further comprising rotating the endoscope sheath from a first viewing angle to a second viewing angle.

* * * * *